United States Patent
Lin

(10) Patent No.: US 10,058,403 B1
(45) Date of Patent: Aug. 28, 2018

(54) DENTAL CLAMPING APPARATUS AND OPERATING METHOD THEREOF

(71) Applicant: CHILIAD BIOMEDICAL TECHNOLOGY CO., LTD., Taichung (TW)

(72) Inventor: Chun-Jung Lin, Taichung (TW)

(73) Assignee: CHILIAD BIOMEDICAL TECHNOLOGY CO., LTD., Taichung (TW)

( * ) Notice: Subject to any disclaimer, the term of this patent is extended or adjusted under 35 U.S.C. 154(b) by 0 days.

(21) Appl. No.: 15/725,270

(22) Filed: Oct. 4, 2017

(30) Foreign Application Priority Data

Jun. 12, 2017 (CN) .......................... 2017 1 0436495

(51) Int. Cl.
*B23B 31/20* (2006.01)
*A61C 8/00* (2006.01)

(52) U.S. Cl.
CPC .......... *A61C 8/0089* (2013.01); *B23B 31/201* (2013.01); *Y10T 279/17538* (2015.01); *Y10T 279/17547* (2015.01)

(58) Field of Classification Search
CPC ............... A61C 8/0089; B23B 31/201; Y10T 279/17529; Y10T 279/17538; Y10T 279/17547
See application file for complete search history.

(56) References Cited

U.S. PATENT DOCUMENTS

| | | | | |
|---|---|---|---|---|
| 1,361,177 A * | 12/1920 | Peterson | ................. | F16C 19/10 384/614 |
| 1,876,950 A * | 9/1932 | Jaques | ............... | A61C 13/0003 433/154 |
| 2,162,856 A * | 6/1939 | Nitsch | .................... | B23Q 3/067 269/243 |
| 2,436,848 A * | 3/1948 | Benjamin | ............. | B23B 31/201 279/50 |
| 2,833,546 A * | 5/1958 | Johnson | ................ | B23B 31/201 279/51 |
| 3,042,418 A * | 7/1962 | Sorsa | ..................... | B23B 31/201 279/18 |
| 2002/0053772 A1* | 5/2002 | Selb | ....................... | B23B 31/201 279/53 |
| 2003/0188434 A1* | 10/2003 | Chiu | ..................... | B23D 51/10 30/144 |

(Continued)

*Primary Examiner* — Daniel Howell
*Assistant Examiner* — Paul M Janeski
(74) *Attorney, Agent, or Firm* — CKC & Partners Co., Ltd.

(57) ABSTRACT

A rotating member of a dental clamping apparatus is movably connected to a body and disposed in a through hole. A hole diameter is located on an inner side of a clamping member and is corresponding to an elastic abutting slope. The clamping member is movably connected to the rotating member. A first blocking member disposed in a first blocking hole is engaged with an annular groove so as to rotate the rotating member relative to the body. A second blocking member disposed in a second blocking hole is engaged with an axial track so as to move the clamping member along an axial direction relative to the body. The rotating member is rotated relative to the body to axially move the clamping member. The elastic abutting slope is abutted against an annular slope so as to resiliently deform the clamping member to change the hole diameter.

15 Claims, 10 Drawing Sheets

(56) References Cited

U.S. PATENT DOCUMENTS

2004/0093745 A1\* 5/2004 Liao .................. B23D 49/14
 30/519
2009/0071299 A1\* 3/2009 Lin .................. B25B 13/461
 81/177.4

\* cited by examiner

DENTAL CLAMPING APPARATUS AND OPERATING METHOD THEREOF

RELATED APPLICATIONS

This application claims priority to China application No. 201710436495.6, filed on Jun. 12, 2017, which is herein incorporated by reference.

BACKGROUND

Technical Field

The present disclosure relates to a dental clamping apparatus and an operating method thereof. More particularly, the present disclosure relates to a dental clamping apparatus and an operating method thereof which are simple to operate and capable of freely exchanging a variety of abutment assemblies having different specifications.

Description of Related Art

A dental implant surgery provides various methods and apparatus for compensating for the loss of natural teeth. Dental implants are devices that are designed to be screwed into the human jawbone and serve as a mounting for a prosthetic in the shape and color of the tooth it is replacing. The primary advantage of implants over bridgework and partial dentures is that the installation is of a permanent nature and does not require the care, maintenance, comfort problems or adjustment associated with bridgework and dentures. In the procedure of the dental implant surgery, it is usually necessary to use a dental clamping apparatus to hold a replacement member, an abutment assembly or other dental objects, so that the dental clamping apparatus plays an important role in the dental implant surgery.

One conventional dental clamping apparatus uses a spring to axially move a clamping member. The clamping member is abutted against the spring. The spring is configured to apply an elastic force to the clamping member. However, this structure of the conventional dental clamping apparatus is quite complex and is cumbersome and inconvenient to assemble. In addition, the conventional dental clamping apparatus carries only one abutment assembly having one size, and is greatly cumbersome and inconvenient for a user or a physician to exchange a variety of abutment assemblies having different specifications. Therefore, a dental clamping apparatus and an operating method thereof which are simple in operation, assembly, exchange and structure, and capable of freely exchanging a variety of abutment assemblies having different specifications are commercially desirable.

SUMMARY

According to one aspect of the present disclosure, a dental clamping apparatus includes a body, a rotating member, a clamping member, a first blocking member and a second blocking member. The body includes an annular slope, a through hole, a first blocking hole and a second blocking hole. The rotating member is movably connected to the body and disposed in the through hole. The rotating member includes an annular groove corresponding to the first blocking hole. The clamping member is disposed in the through hole. The clamping member includes an axial track, an elastic abutting slope and a hole diameter. The elastic abutting slope is located on an outer side of the clamping member. The hole diameter is located on an inner side of the clamping member and is corresponding to the elastic abutting slope. The clamping member is movably connected to the rotating member. The first blocking member is disposed in the first blocking hole. The first blocking member is engaged with the annular groove so as to rotate the rotating member relative to the body. The second blocking member is disposed in the second blocking hole. The second blocking member is engaged with the axial track so as to move the clamping member along an axial direction relative to the body. The rotating member is rotated relative to the body to axially move the clamping member. The elastic abutting slope is abutted against the annular slope so as to resiliently deform the clamping member to change the hole diameter.

According to another aspect of the present disclosure, a dental clamping apparatus includes a body, a rotating member, a clamping member, a ball bearing, a first blocking member and a second blocking member. The body includes an annular slope, a through hole, a first blocking hole and a second blocking hole. The rotating member is movably connected to the body and disposed in the through hole. The rotating member includes an annular groove corresponding to the first blocking hole. The clamping member is disposed in the through hole. The clamping member includes an axial track, an elastic abutting slope and a hole diameter. The elastic abutting slope is located on an outer side of the clamping member. The hole diameter is located on an inner side of the clamping member and is corresponding to the elastic abutting slope. The clamping member is movably connected to the rotating member. The ball bearing is rotatably connected between the rotating member and the body. The first blocking member is disposed in the first blocking hole. The first blocking member is engaged with the annular groove so as to rotate the rotating member relative to the body. The second blocking member is disposed in the second blocking hole. The second blocking member is engaged with the axial track so as to move the clamping member along an axial direction relative to the body. The rotating member is rotated relative to the body to axially move the clamping member. The elastic abutting slope is abutted against the annular slope so as to resiliently deform the clamping member to change the hole diameter.

According to further another aspect of the present disclosure, an operating method of the dental clamping apparatus provides a clamping member tightening and loosening step. The clamping member tightening and loosening step is for rotating the rotating member relative to the body to axially move the clamping member, and the elastic abutting slope is abutted against the annular slope so as to resiliently deform the clamping member to change the hole diameter. When the hole diameter is greater than a diameter of a replacement member, the replacement member is loosened by the clamping member and detachably connected to an abutment assembly. When the hole diameter is equal to or smaller than the diameter of the replacement member, the replacement member is tightened by the clamping member.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
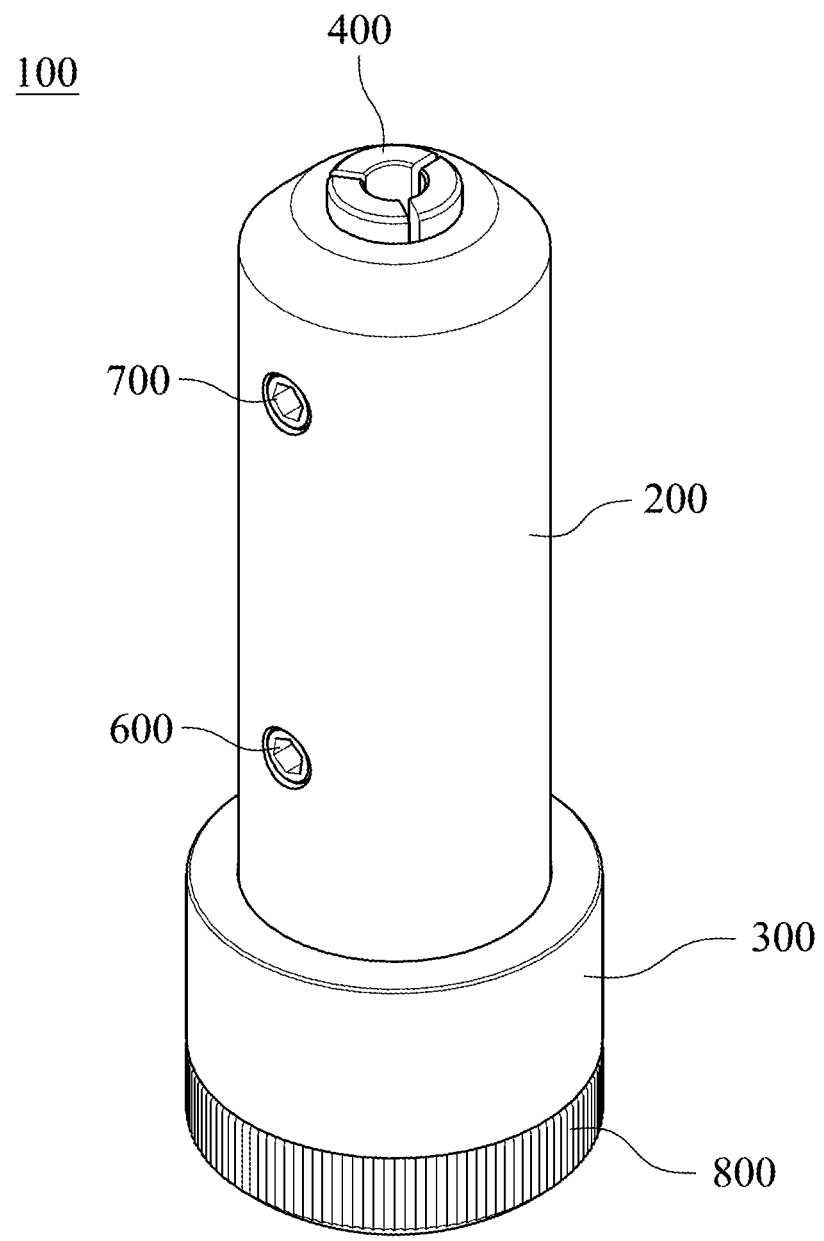
FIG. 1 shows a schematic view of a dental clamping apparatus according to one embodiment of the present disclosure.
Figure 2:
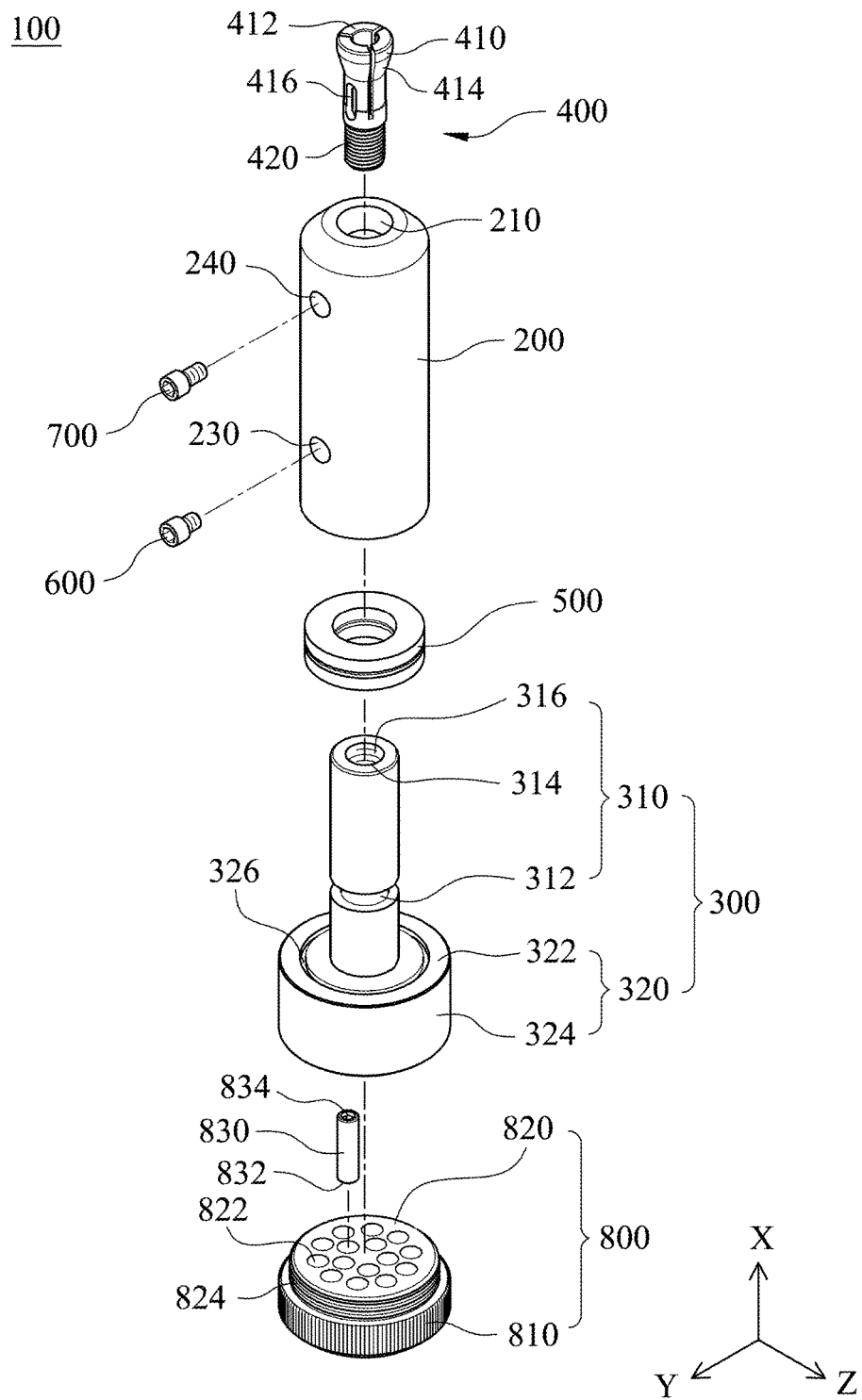
FIG. 2 shows one exploded view of the dental clamping apparatus of FIG. 1.
Figure 3:
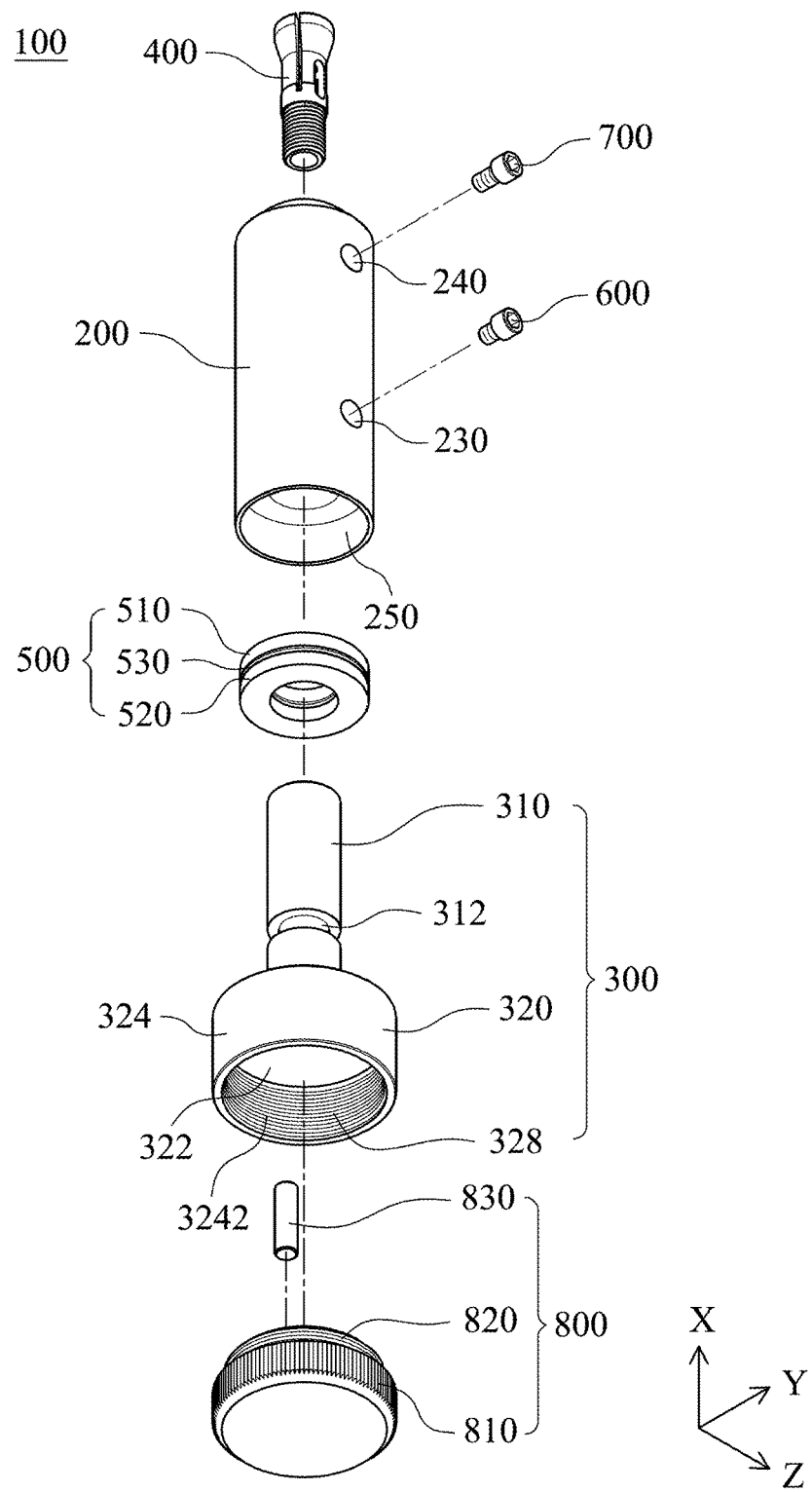
FIG. 3 shows another exploded view of the dental clamping apparatus of FIG. 1.
Figure 4:
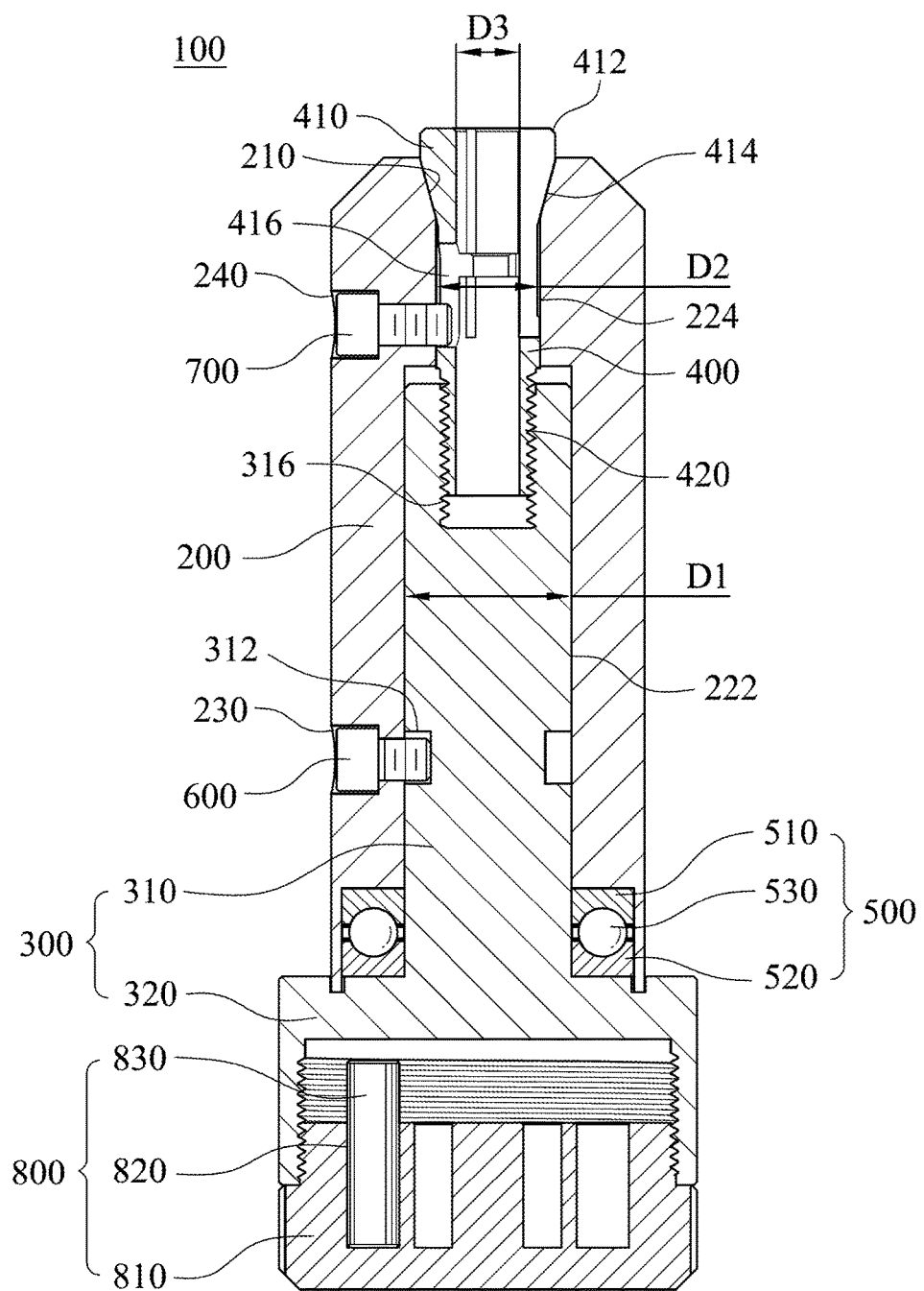
FIG. 4 shows a cross-sectional view of the dental clamping apparatus of FIG. 1.
Figure 5:
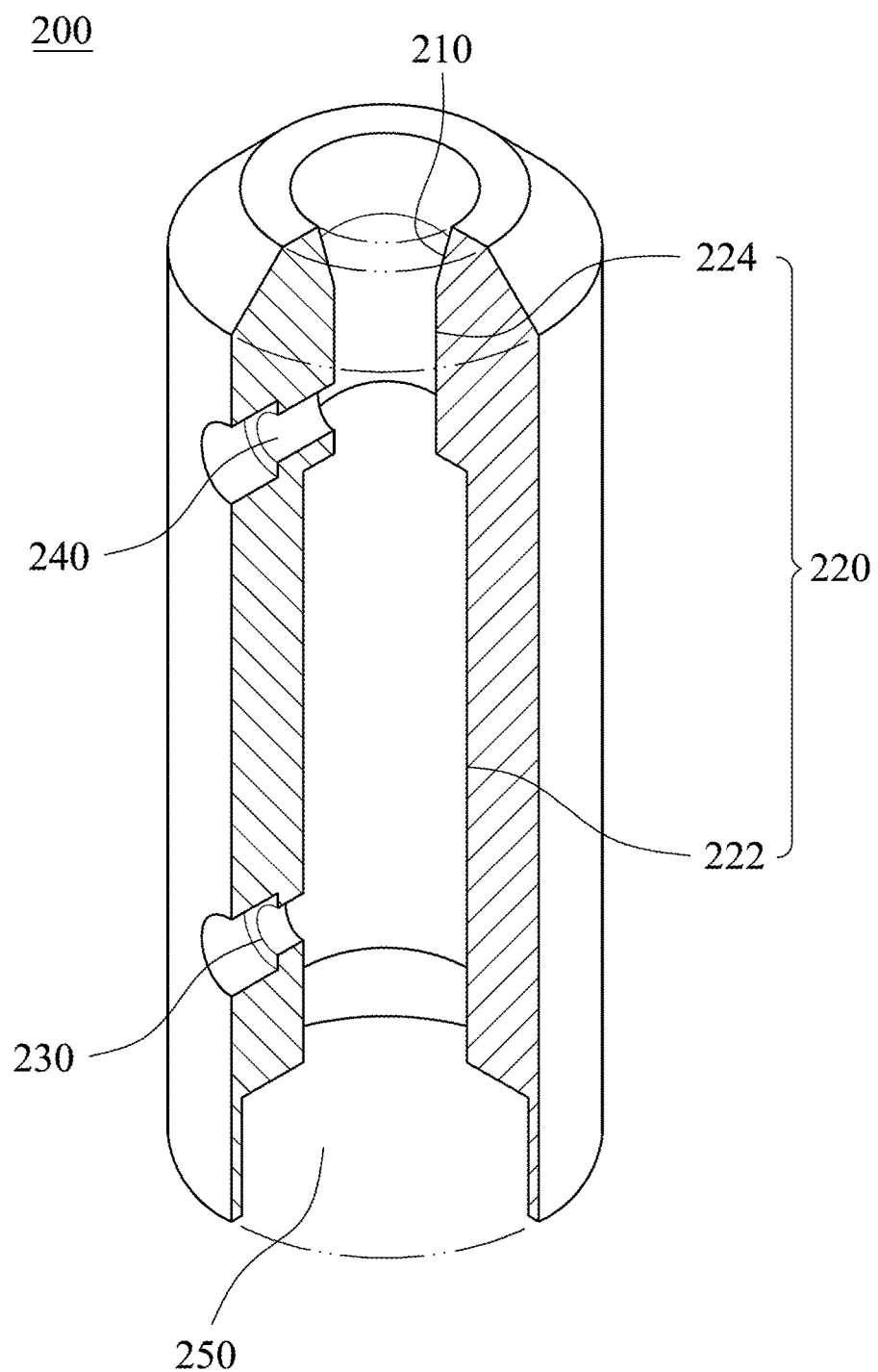
FIG. 5 shows a cross-sectional view of a body of the dental clamping apparatus of FIG. 1.
Figure 6:
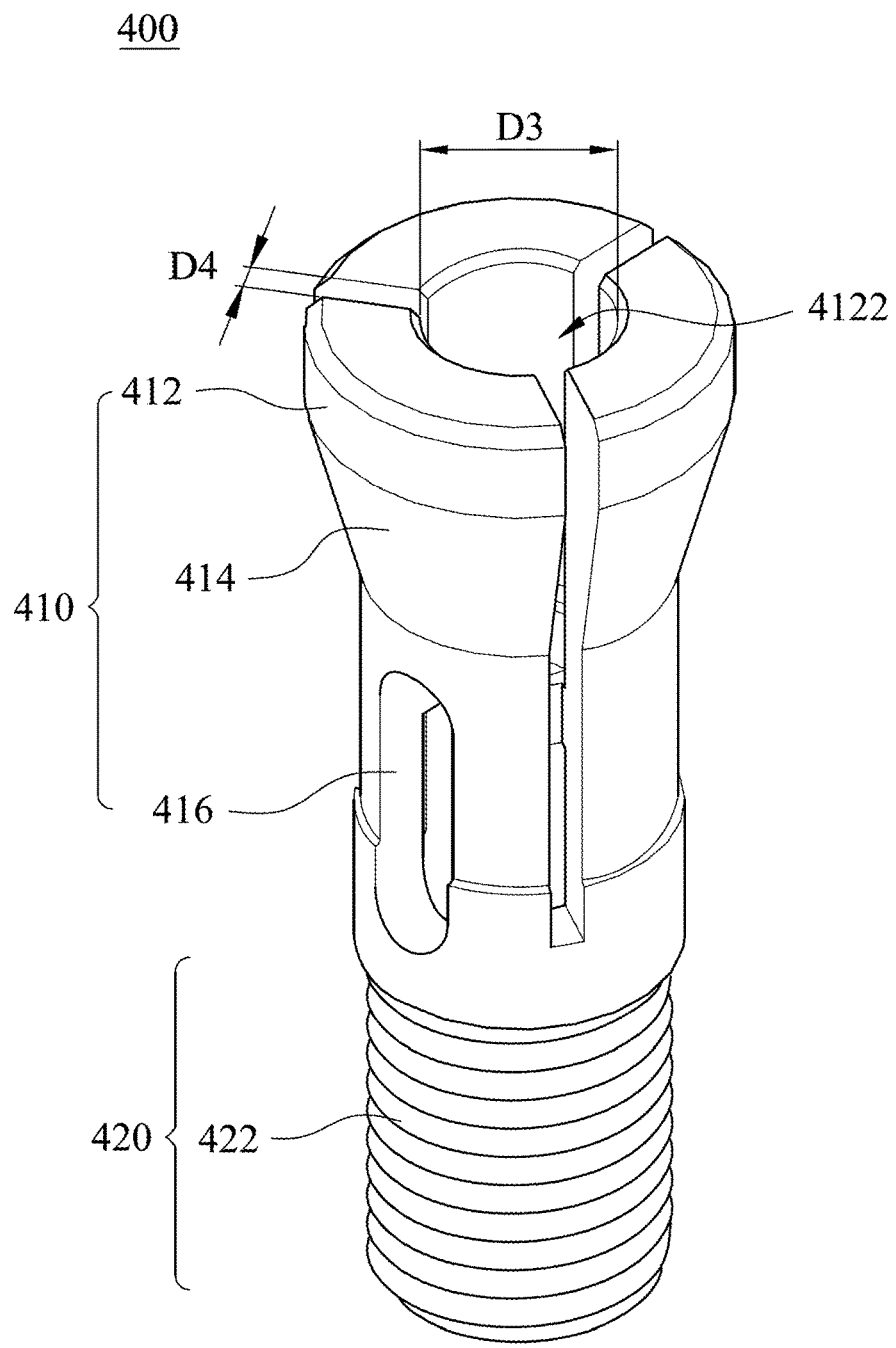
FIG. 6 shows a schematic view of a clamping member of the dental clamping apparatus of FIG. 1.
Figure 7:
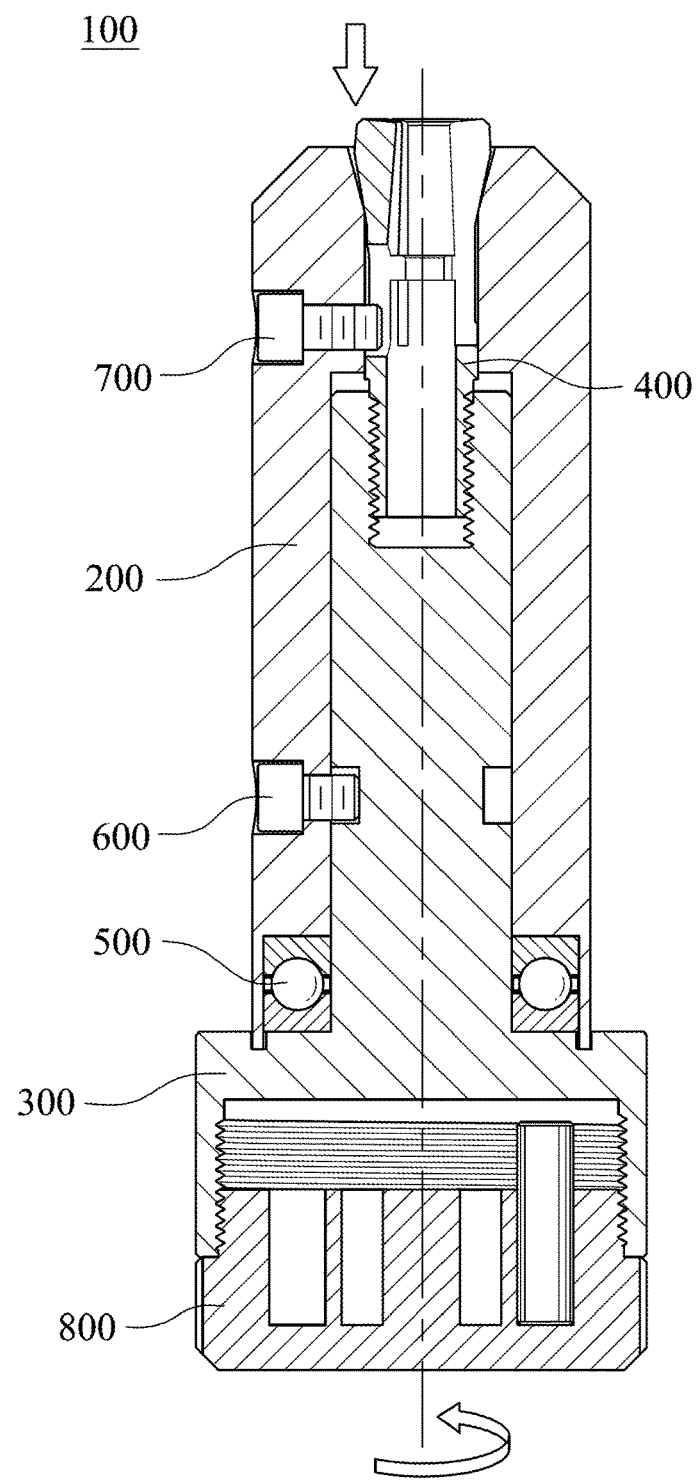
FIG. 7 shows a schematic view of an operation of the dental clamping apparatus of FIG. 1.

FIG. 1 shows a schematic view of a dental clamping apparatus 100 according to one embodiment of the present disclosure; FIG. 2 shows one exploded view of the dental clamping apparatus 100 of FIG. 1; FIG. 3 shows another exploded view of the dental clamping apparatus 100 of FIG. 1; FIG. 4 shows a cross-sectional view of the dental clamping apparatus 100 of FIG. 1; FIG. 5 shows a cross-sectional view of a body 200 of the dental clamping apparatus 100 of FIG. 1; FIG. 6 shows a schematic view of a clamping member 400 of the dental clamping apparatus 100 of FIG. 1; and FIG. 7 shows a schematic view of an operation of the dental clamping apparatus 100 of FIG. 1. The dental clamping apparatus 100 is used for clamping an abutment assembly. The dental clamping apparatus 100 includes the body 200, a rotating member 300, the clamping member 400, a ball bearing 500, a first blocking member 600, a second blocking member 700 and a replacement seat assembly 800.

The body 200 has a hollow cylindrical shape and includes an annular slope 210, a through hole 220, a first blocking hole 230 and a second blocking hole 240 and a bearing accommodating space 250. The annular slope 210 is located at a front end of the body 200 and is inclined outwardly. In other words, the annular slope 210 is gradually reduced from outside towards inside and has a cone shape. The through hole 220 is communicated with the annular slope 210. An extending direction of the through hole 220 is parallel to an axial direction and an X-axis direction. The through hole 220 includes a first hole 222 and a second hole 224. The first hole 222 has a first diameter D1. The first blocking hole 230 is perpendicularly communicated with the first hole 222 and faced towards a first radial direction. The first radial direction is perpendicular to the axial direction and parallel to a Y-Z plane. In addition, the second hole 224 is communicated with the first hole 222 and has a second diameter D2. The second hole 224 is located between the first hole 222 and the annular slope 210. The second diameter D2 is smaller than the first diameter D1. The second blocking hole 240 is perpendicularly communicated with the second hole 224 and faced towards a second radial direction. The second radial direction is perpendicular to the axial direction and parallel to a Y-Z plane. Moreover, the bearing accommodating space 250 is communicated with the first hole 222 and located at a rear end of the body 200. The bearing accommodating space 250 has a cylindrical shape, and a diameter of the bearing accommodating space 250 is greater than the first diameter D1 of the first hole 222.

The rotating member 300 is movably connected to the body 200 and disposed in the through hole 220 and the bearing accommodating space 250. The rotating member 300 includes a rotating shaft 310 and a rotating seat 320. The rotating shaft 310 includes an annular groove 312, a rotating hole 314 and an internal thread 316. The rotating shaft 310 has a cylindrical shape and is passed through the bearing accommodating space 250. The annular groove 312 is concavely disposed an outer side wall of the rotating shaft 310. The rotating hole 314 is located at a front end of the rotating shaft 310. The internal thread 316 is disposed in the rotating hole 314. When the rotating member 300 is connected to the body 200, the rotating shaft 310 is disposed through the first hole 222. The annular groove 312 is corresponding to the first blocking hole 230. Furthermore, the rotating seat 320 is connected to a rear end of the rotating shaft 310. The rotating seat 320 has the cylindrical shape, and a diameter of the rotating seat 320 is greater than a diameter of the rotating shaft 310. In detail, the rotating seat 320 includes an end wall 322 and a side wall 324. The end wall 322 includes a limiting ring groove 326 movably engaged with one end of the body 200 so as to limit relative displacement between the body 200 and the rotating member 300. The limiting ring groove 326 has a ring shape and is correspondingly connected to the rear end of the body 200. A thickness of the rear end of the body 200 is equal to or smaller than a width of the limiting ring groove 326, so that the body 200 and the rotating member 300 can smoothly rotate relative to each other. Additionally, the side wall 324 is connected to the end wall 322 to form an accommodating space 328. The accommodating space 328 is corresponding to the replacement seat assembly 800. The side wall 324 has a sidewall internal thread 3242 for connecting to the replacement seat assembly 800.

The clamping member 400 is disposed in the through hole 220. The clamping member 400 includes a resilient abutting portion 410 and a connecting portion 420. The resilient abutting portion 410 includes three resilient abutting members 412, an elastic abutting slope 414, an axial track 416 and the hole diameter D3. The three resilient abutting members 412 connected to the connecting portion 420 are circularly arranged to form an annular channel 4122. The annular channel 4122 has the hole diameter D3 located on an inner side of the clamping member 400 (i.e., the hole diameter D3 is located inside of the resilient abutting portion 410). Two of the three resilient abutting members 412 are spaced by a distance D4. In addition, the axial track 416 is disposed on one of the three resilient abutting members 412. The axial track 416 is communicated with the annular channel 4122 and is parallel to the axial direction. The elastic abutting slope 414 is formed outside of the three resilient abutting members 412 and inclined outwardly in the axial direction. The elastic abutting slope 414 is connected to the annular slope 210 of the body 200. The hole diameter D3 is corresponding to the three resilient abutting members 412 and the elastic abutting slope 414. The elastic abutting slope 414 is located on an outer side of the clamping member 400 (i.e., the elastic abutting slope 414 is located outside of the resilient abutting portion 410). When the elastic abutting slope 414 is abutted against the annular slope 210, the resilient abutting members 412 move closer to each other, thus decreasing the hole diameter D3. On the contrary, when the elastic abutting slope 414 is not abutted against the annular slope 210 or the force exerted by the annular slope 210 becomes smaller, the resilient abutting members 412 move away from to each other, thus increasing the hole diameter D3 (i.e., the resilient abutting members 412 return to the original appearance). In other words, the maximum value of the hole diameter D3 is equal to the diameter of the annular channel 4122 when the resilient abutting members 412 is not abutted against the annular slope 210. The minimum value of the hole diameter D3 is equal to the diameter of the annular channel 4122 when the resilient abutting members 412 is abutted against the annular slope 210, and the distance D4 is equal to zero. Therefore, the clamping member 400 utilizes the resilient deformation produced by the elastic abutting slope 414 and the annular slope 210 to change the hole diameter D3 and the distance D4. The structure of the clamping member 400 can clamp a variety of objects having different sizes within a certain range. Moreover, the clamping member 400 is movably connected to the rotating member 300. In detail, the connecting portion 420 of the clamping member 400 is movably connected to the rotating member 300. The connecting portion 420 has an external thread 422 corresponding to the internal thread 316, and the external thread 422 is correspondingly screwed into the internal thread 316. The connecting portion 420 is disposed in the through hole 220. One end of the connecting portion 420 is connected to the resilient abutting portion 410, and the other end of the connecting portion 420 is movably connected to the rotating member 300 via the external thread 422 and the internal thread 316.

The ball bearing 500 is rotatably connected between the rotating member 300 and the body 200. In detail, the ball bearing 500 is surroundedly attached to the rotating shaft 310 and connected to the rotating seat 320. The ball bearing 500 has a ring shape and a flaky shape. The ball bearing 500 is disposed in the bearing accommodating space 250. The ball bearing 500 includes a first annular member 510, a second annular member 520 and a ball assembly 530. The first annular member 510 is connected to the body 200 and synchronously moved with the body. The second annular member 520 is connected to the rotating member 300 and synchronously moved with the rotating seat 320 of the rotating member 300. The ball assembly 530 is located between the first annular member 510 and the second annular member 520. The first annular member 510 is moved relative to the second annular member 520 via the ball assembly 530, so that the body 200 and the rotating member 300 rotate relative to each other. Hence, the dental clamping apparatus 100 of the present disclosure uses the arrangement of the ball bearing 500 to reduce a rotational resistance between the body 200 and the rotating member 300, thereby allowing the user to effortlessly and smoothly operate the dental clamping apparatus 100. Additionally, if the dental clamping apparatus 100 is manufactured without the ball bearing 500, the body 200 and the rotating member 300 can still rotate relative to each other to axially move the clamping member 400 so as to reduce the total weight, complexity and manufacturing cost of the dental clamping apparatus 100.

The first blocking member 600 is disposed in the first blocking hole 230. The second blocking member 700 is disposed in the second blocking hole 240. The first blocking member 600 is engaged with the annular groove 312 of the rotating member 300 so as to rotate the rotating member 300 relative to the body 200. In other words, the first blocking member 600 can prevent the rotating member 300 from breaking away from the body 200 and avoid the rotating member 300 moving along the axial direction. In addition, the second blocking member 700 is engaged with the axial track 416 of the clamping member 400 so as to move the clamping member 400 along an axial direction relative to the body 200, that is to say, the second blocking member 700 can prevent the clamping member 400 from breaking away from the body 200 and avoid the clamping member 400 rotating relative to the body 200. Furthermore, the first blocking member 600 and the second blocking member 700 may be screws or plugs. In FIGS. 2 and 3, the first blocking member 600 and the second blocking member 700 are both hexagon socket screws which can be disassembled by a corresponding hexagonal wrench. The first radial direction of the first blocking hole 230 is the same as the second radial direction of the second blocking hole 240. Certainly, the first radial direction can be different from the second radial direction as long as the first radial direction and the second radial direction are parallel to the Y-Z plane according to the application needs. Therefore, the dental damping apparatus 100 of the present disclosure utilizes the first blocking member 600 and the second blocking member 700 to limit the moving directions of the body 200, the rotating member 300 and the damping member 400, so that the rotating member 300 is rotated relative to the body 200 to axially move the clamping member 400. The elastic abutting slope 414 is abutted against the annular slope 210 so as to resiliently deform the clamping member 400 to change the hole diameter D3, thereby allowing the user to freely exchange a variety of abutment assemblies having different specifications.

The replacement seat assembly 800 is detachably connected to the rotating seat 320 of the rotating member 300. The replacement seat assembly 800 includes a rotating portion 810, an accommodating seat 820 and a plurality of replacement members 830. The rotating portion 810 has a rugged surface for rotating the replacement seat assembly 800 by a user. The accommodating seat 820 is connected to the rotating portion 810 and includes a plurality of accommodating grooves 822. Each of the replacement members 830 is detachably connected to one of the accommodating grooves 822 (i.e., the replacement members 830 are detachably connected to the accommodating grooves 822, respectively). Each of the replacement members 830 has an accommodating end 832 and an engaging end 834. A shape of the accommodating end 832 is corresponding to a shape of one of the accommodating grooves 822, and a shape of the engaging end 834 is corresponding to a shape of the abutment assembly. In one embodiment, the accommodating grooves 822 and the accommodating ends 832 of the replacement members 830 can all be in the same shape. The number of the accommodating grooves 822 is 15, as shown in FIG. 2. The replacement seat assembly 800 is configured to replace a plurality of abutment assemblies with each other so as to clamp one of the abutment assemblies by the clamping member 400. The shapes of the engaging ends 834 of the replacement members 830 are corresponding to the shapes of the abutment assemblies, respectively. The shapes and sizes of the engaging ends 834 are different from each other. The abutment assemblies having fifteen kinds of different specifications can be disposed in the accommodating grooves 822 of the replacement seat assembly 800. In addition, the accommodating space 328 of the rotating member 300 is corresponding to the accommodating seat 820 of the replacement seat assembly 800. The sidewall internal thread 3242 is formed inside the side wall 324. The accommodating seat 820 has an accommodating external thread 824 corresponding to sidewall internal thread 3242, and the accommodating external thread 824 is correspondingly screwed into the sidewall internal thread 3242. When the replacement seat assembly 800 is connected to the rotating member 300, the accommodating seat 820 and the replacement members 830 are located in the accommodating space 328. Accordingly, the replacement seat assembly 800 of the present disclosure can cooperate with the rotating member 300 to carry a variety of replacement members 830 having different specifications, so that it is extremely portable and convenient for the user to exchange the replacement members 830, and the proposed structure is very suitable for use in mobile medical applications. Moreover, the replacement members 830 of the present disclosure are corresponding to a variety of abutment assemblies having different specifications, respectively, thus allowing the user to freely exchange the desired abutment assemblies.

Figure 8:
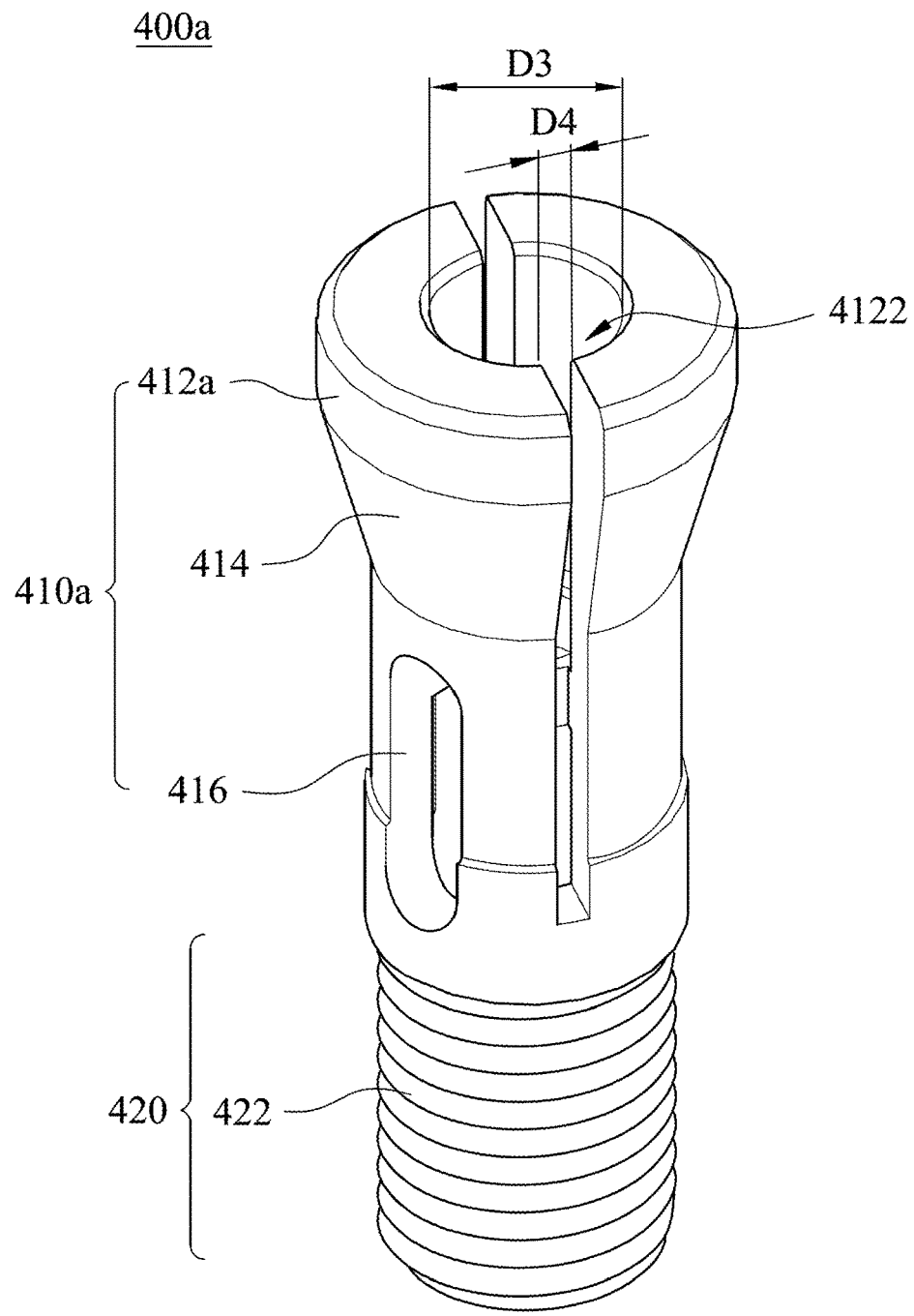
FIG. 8 shows a schematic view of a clamping member of a dental clamping apparatus according to another embodiment of the present disclosure.

FIG. 8 shows a schematic view of a clamping member 400a of a dental clamping apparatus 100 according to another embodiment of the present disclosure. The clamping member 400a includes a resilient abutting portion 410a and a connecting portion 420. The detail of the connecting portion 420 is the same as the embodiment of FIG. 6. The resilient abutting portion 410a includes two resilient abutting members 412a, an elastic abutting slope 414, an axial track 416 and the hole diameter D3. Each of the two resilient abutting members 412a has a half arc-shape. The two resilient abutting members 412a connected to the connecting portion 420 are circularly arranged to form an annular channel 4122. The annular channel 4122 has the hole diameter D3 located on the inner side of the clamping member 400 (i.e., the hole diameter D3 is located inside of the resilient abutting portion 410a). The two resilient abutting members 412a are spaced by a distance D4. In addition, a pitch of the external thread 422, an inclination angle of the elastic abutting slope 414 and a size of the distance D4 affect the magnitude and the rate of change of the hole diameter D3, and are determined by the manufacturer to meet the market requirements. The number of the resilient abutting members 412a of the resilient abutting portion 410a and the number of the resilient abutting members 412 of the resilient abutting portion 410 may be equal to or greater than 2. The more the number of the resilient abutting members 412, 412a is, the more the complexity of the manufacturing process is. More preferably, the number of the resilient abutting members 412a is 2, as shown in FIG. 8. Most preferably, the number of the resilient abutting members 412 is 3, as shown in FIG. 6.

Figure 9:
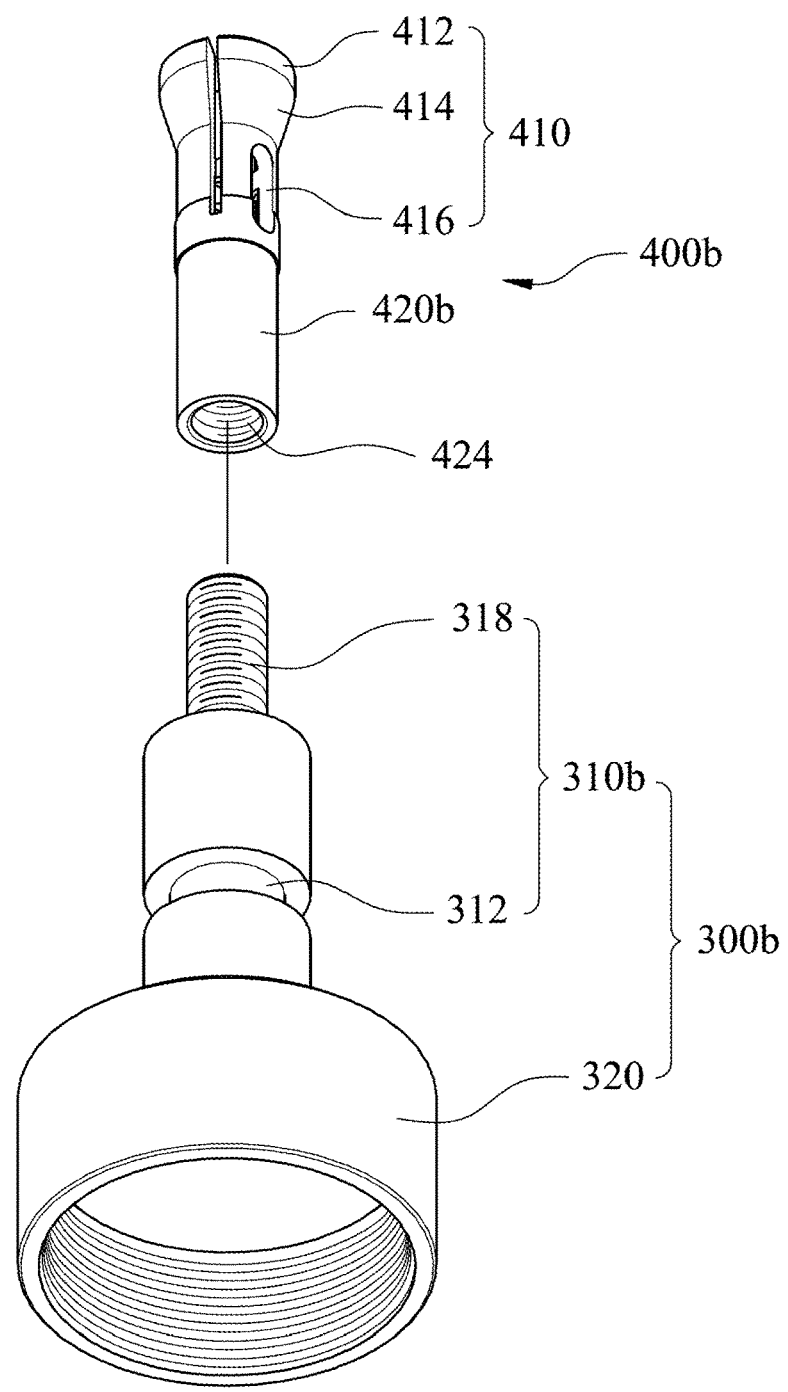
FIG. 9 shows a schematic view of a clamping member and a rotating member of a dental clamping apparatus according to further another embodiment of the present disclosure.

FIG. 9 shows a schematic view of a clamping member 400b and a rotating member 300b of a dental clamping apparatus 100 according to further another embodiment of the present disclosure. In FIGS. 2, 4 and 9, the rotating member 300b is movably connected to the body 200 and disposed in the through hole 220 and the bearing accommodating space 250. The rotating member 300b includes a rotating shaft 310b and a rotating seat 320. The rotating shaft 310b includes an annular groove 312 and a convex thread 318. The rotating shaft 310b has a cylindrical shape and is passed through the bearing accommodating space 250. The annular groove 312 is concavely disposed an outer side wall of the rotating shaft 310b. The convex thread 318 is located at a front end of the rotating shaft 310b. In addition, the clamping member 400b is disposed in the through hole 220. The clamping member 400b includes a resilient abutting portion 410 and a connecting portion 420b. The detail of the resilient abutting portion 410 is the same as the resilient abutting portion 410 of FIG. 2. The connecting portion 420b is movably connected to the rotating member 300b. The connecting portion 420b has a concave thread 424 corresponding to the convex thread 318. The concave thread 424 is located at a rear end of the clamping member 400b. The concave thread 424 is correspondingly screwed into the convex thread 318 of the rotating member 300b. The connecting portion 420b is disposed in the through hole 220. One end of the connecting portion 420b is connected to the resilient abutting portion 410, and the other end of the connecting portion 420b is movably connected to the rotating member 300 via the concave thread 424 and the convex thread 318.

Figure 10:
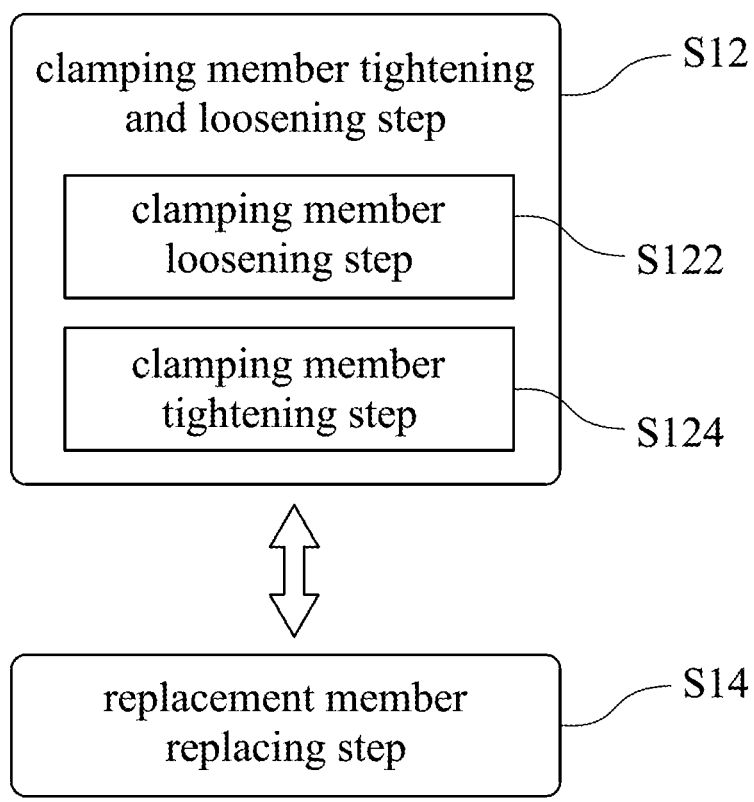
FIG. 10 shows a flow chart of an operating method of a dental clamping apparatus according to one embodiment of the present disclosure.

FIG. 10 shows a flow chart of an operating method 900 of a dental clamping apparatus 100 according to one embodiment of the present disclosure. In FIGS. 2, 6 and 10, the operating method 900 of a dental clamping apparatus 100 provides a clamping member tightening and loosening step S12 and a replacement member replacing step S14. The clamping member tightening and loosening step S12 is for rotating the rotating member 300 relative to the body 200 to axially move the clamping member 400, and the elastic abutting slope 414 is abutted against the annular slope 210 so as to resiliently deform the clamping member 400 to change the hole diameter D3. In detail, the clamping member tightening and loosening step S12 includes a clamping member loosening step S122 and a clamping member tightening step S124. The clamping member loosening step S122 is for rotating the rotating member 300 relative to the body 200 to move the clamping member 400 in a positive X-axis direction to increase the hole diameter D3, so that the clamping member 400 loosens the replacement member 830. When the hole diameter D3 is greater than the diameter of the replacement member 830, the replacement member 830 is loosened by the clamping member 400. Moreover, the clamping member tightening step S124 is for rotating the rotating member 300 relative to the body 200 to move the clamping member 400 in a negative X-axis direction to decrease the hole diameter D3, so that the clamping member 400 tightens the replacement member 830. When the hole diameter D3 is equal to or smaller than the diameter of the replacement member 830, the replacement member 830 is tightened by the clamping member 400 and detachably connected to the abutment assembly. The abutment assembly includes an abutment and an adjustable plastic member. The abutment can be correspondingly screwed onto the replacement member 830. The adjustable plastic member is tightly connected to the abutment, so that the abutment is located between the replacement member 830 and the adjustable plastic member. The adjustable plastic member is made of a medical material selected from the group consisting of Polymethylmethacrylate (PMMA) and Polyetheretherketone (PEEK). The hardness of the adjustable plastic member is much lower than the hardness of metal so as to be easily grinded or cut by an instrument. The instrument is made of metal and may be a blade or a drill. Furthermore, the replacement member replacing step S14 is for separating a replacement seat assembly 800 from the rotating member 300, and then moving the replacement member 830 from the replacement seat assembly 800 to the clamping member 400. The steps of the operating method 900 of the dental clamping apparatus 100 are carried out in order of the clamping member loosening step S122, the replacement member replacing step S14 and the clamping member tightening step S124.

For one example, there is no replacement member 830 clamped by the clamping member 400 at the beginning. The rotating member 300 is rotated relative to the body 200 to increase the hole diameter D3 in the clamping member loosening step S122. A desired replacement member 830 is disposed in one of the accommodating grooves 822. When the user wants to install the desired replacement member 830 on the clamping member 400, the replacement seat assembly 800 is rotated by the user via the rotating portion 810 to separate the replacement seat assembly 800 from the rotating member 300. In the replacement member replacing step S14, the desired replacement member 830 is taken out from the corresponding accommodating groove 822 and then is disposed into the annular channel 4122 of the clamping member 400 by the user. In the clamping member tightening step S124, the rotating member 300 is rotated relative to the body 200 to decrease the hole diameter D3, so that the replacement member 830 is stably tightened by the clamping member 400.

For another example, there is a replacement member 830a clamped by the clamping member 400, and a desired replacement member 830b is disposed in one of the accommodating grooves 822 at the beginning. When the user wants to exchange the replacement member 830a with the desired replacement member 830b, the rotating member 300 is rotated relative to the body 200 to increase the hole diameter D3 in the clamping member loosening step S122. Then, the replacement member 830a is taken out from the clamping member 400, and the replacement seat assembly 800 is rotated by the user via the rotating portion 810 to separate the replacement seat assembly 800 from the rotating member 300. In the replacement member replacing step S14, the desired replacement member 830b is taken out from the corresponding accommodating groove 822 and then is disposed on the clamping member 400 by the user, so that the replacement member 830a is exchanged with the desired replacement member 830b. In the clamping member tightening step S124, the rotating member 300 is rotated relative to the body 200 to decrease the hole diameter D3, so that the desired replacement member 830b is stably tightened by the clamping member 400. Therefore, the dental clamping apparatus 100 employs an exchangeable structure to allowing the user to freely exchange the desired abutment assemblies and the replacement members 830a, 830b. Furthermore, the replacement seat assembly 800 of the present disclosure can cooperate with the rotating member 300 to carry a variety of replacement members 830a, 830b having different specifications. The rotating member 300 combined with the clamping member 400 and the body 200 can change the hole diameter D3 of the clamping member 400 to tighten or loosen the replacement members 830a, 830b having different sizes, thereby solving problems that a conventional dental clamping apparatus carries only one abutment assembly having one size, and is cumbersome and inconvenient to exchange a variety of abutment assemblies having different specifications.

According to the aforementioned embodiments and examples, the advantages of the present disclosure are described as follows.

1. The replacement seat assembly of the present disclosure can cooperate with the rotating member to carry a variety of replacement members having different specifications, so that it is extremely portable and convenient for the user to exchange the replacement members. The proposed structure is very suitable for use in mobile medical applications.

2. The replacement members of the present disclosure are corresponding to a variety of abutment assemblies having different specifications, respectively, thus allowing the user to freely exchange the desired abutment assemblies.

3. The dental clamping apparatus of the present disclosure uses the arrangement of the ball bearing to reduce a rotational resistance between the body and the rotating member, thereby allowing the user to effortlessly and smoothly operate the dental clamping apparatus.

4. The combination of the replacement seat assembly, the rotating member, the clamping member and the body of the present disclosure can change the hole diameter of the clamping member to tighten or loosen the replacement members having different sizes, thereby solving problems that the conventional dental clamping apparatus carries only one abutment assembly having one size, and is cumbersome and inconvenient to exchange a variety of abutment assemblies having different specifications.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A dental clamping apparatus, comprising:
  a body comprising an annular slope, a through hole, a first blocking hole and a second blocking hole;
  a rotating member movably connected to the body and disposed in the through hole, wherein the rotating member comprises an annular groove corresponding to the first blocking hole;
  a clamping member disposed in the through hole, wherein the clamping member comprises an axial track, an elastic abutting slope and a hole diameter, the elastic abutting slope is located on an outer side of the clamping member, the hole diameter is located on an inner side of the clamping member and is corresponding to the elastic abutting slope, and the clamping member is movably connected to the rotating member;
  a first blocking member disposed in the first blocking hole, wherein the first blocking member is engaged with the annular groove so as to rotate the rotating member relative to the body;
  a second blocking member disposed in the second blocking hole, wherein the second blocking member is engaged with the axial track so as to move the clamping member along an axial direction relative to the body; and
  a replacement seat assembly detachably connected to the rotating member and comprising:
    a rotating portion;
    an accommodating seat connected to the rotating portion and comprising a plurality of accommodating grooves; and
    a plurality of replacement members detachably connected to the accommodating grooves, respectively, wherein each of the replacement members has an accommodating end and an engaging end, a shape of the accommodating end is corresponding to a shape of one of the accommodating grooves, and a shape of the engaging end is corresponding to a shape of an abutment assembly;
  wherein the rotating member is rotated relative to the body to axially move the clamping member, the elastic abutting slope is abutted against the annular slope so as to resiliently deform the clamping member to change the hole diameter;

wherein the rotating member further comprises:
an end wall comprising a limiting ring groove movably engaged with one end of the body so as to limit relative displacement between the body and the rotating member; and
a side wall connected to the end wall to form an accommodating space, wherein the accommodating space is corresponding to the accommodating seat, the side wall has a sidewall internal thread, the accommodating seat has an accommodating external thread, and the accommodating external thread is correspondingly screwed into the sidewall internal thread;
wherein the replacement seat assembly is configured to replace a plurality of abutment assemblies with each other so as to clamp one of the abutment assemblies by the clamping member;
wherein the rotating portion has a rugged surface.

2. The dental clamping apparatus of claim 1, wherein,
the rotating member has an internal thread; and
the clamping member has an external thread corresponding to the internal thread, and the external thread is correspondingly screwed into the internal thread.

3. The dental clamping apparatus of claim 2, wherein the rotating member further comprises:
a rotating shaft comprising the annular groove and a rotating hole, and having a cylindrical shape, wherein the internal thread is disposed in the rotating hole, and the rotating hole is located at a front end of the rotating shaft; and
a rotating seat connected to a rear end of the rotating shaft, wherein the rotating seat has the cylindrical shape, and a diameter of the rotating seat is greater than a diameter of the rotating shaft.

4. The dental clamping apparatus of claim 1, wherein the clamping member further comprises:
a resilient abutting portion comprising the axial track, the elastic abutting slope and the hole diameter, wherein the axial track is parallel to the axial direction, the elastic abutting slope is located outside of the resilient abutting portion, and the hole diameter is located inside of the resilient abutting portion; and
a connecting portion disposed in the through hole, wherein one end of the connecting portion is connected to the resilient abutting portion, and the other end of the connecting portion is movably connected to the rotating member.

5. The dental clamping apparatus of claim 4, wherein the resilient abutting portion further comprises:
at least two resilient abutting members spaced by a distance, wherein the two resilient abutting members are both connected to the connecting portion, the axial track is disposed on one of the two resilient abutting members, the elastic abutting slope is formed outside of the two resilient abutting members and inclined outwardly in the axial direction.

6. The dental clamping apparatus of claim 1, wherein the through hole comprises:
a first hole having a first diameter, wherein the first blocking hole is communicated with the first hole and faced towards a first radial direction; and
a second hole communicated with the first hole and having a second diameter, wherein the second diameter is smaller than the first diameter, the second blocking hole is communicated with the second hole and faced towards a second radial direction.

7. An operating method of the dental clamping apparatus of claim 1, comprising:
providing a clamping member tightening and loosening step, wherein the clamping member tightening and loosening step is for rotating the rotating member relative to the body to axially move the clamping member, and the elastic abutting slope is abutted against the annular slope so as to resiliently deform the clamping member to change the hole diameter;
wherein when the hole diameter is greater than a diameter of a replacement member, the replacement member is loosened by the clamping member;
wherein when the hole diameter is equal to or smaller than the diameter of the replacement member, the replacement member is tightened by the clamping member and detachably connected to an abutment assembly.

8. The operating method of the dental clamping apparatus of claim 7, further comprising:
providing a replacement member replacing step, wherein the replacement member replacing step is for separating a replacement seat assembly from the rotating member, and then moving the replacement member from the replacement seat assembly to the clamping member;
wherein the clamping member tightening and loosening step comprises:
providing a clamping member loosening step, wherein the clamping member loosening step is for rotating the rotating member relative to the body to move the clamping member in a positive X-axis direction to increase the hole diameter; and
providing a clamping member tightening step, wherein the clamping member tightening step is for rotating the rotating member relative to the body to move the clamping member in a negative X-axis direction to decrease the hole diameter;
wherein the steps of the operating method are carried out in order of the clamping member loosening step, the replacement member replacing step and the clamping member tightening step.

9. A dental clamping apparatus, comprising:
a body comprising an annular slope, a through hole, a first blocking hole and a second blocking hole;
a rotating member movably connected to the body and disposed in the through hole, wherein the rotating member comprises an annular groove corresponding to the first blocking hole;
a clamping member disposed in the through hole, wherein the clamping member comprises an axial track, an elastic abutting slope and a hole diameter, the elastic abutting slope is located on an outer side of the clamping member, the hole diameter is located on an inner side of the clamping member and is corresponding to the elastic abutting slope, and the clamping member is movably connected to the rotating member;
a ball bearing rotatably connected between the rotating member and the body;
a first blocking member disposed in the first blocking hole, wherein the first blocking member is engaged with the annular groove so as to rotate the rotating member relative to the body;
a second blocking member disposed in the second blocking hole, wherein the second blocking member is engaged with the axial track so as to move the clamping member along an axial direction relative to the body; and a replacement seat assembly detachably connected to the rotating member and comprising:
a rotating portion;
an accommodating seat connected to the rotating portion and comprising a plurality of accommodating grooves; and
a plurality of replacement members detachably connected to the accommodating grooves, respectively, wherein each of the replacement members has an accommodating end and an engaging end, a shape of the accommodating end is corresponding to a shape of one of the accommodating grooves, and a shape of the engaging end is corresponding to the shape of one of a plurality of abutment assemblies;
wherein the rotating member is rotated relative to the body to axially move the clamping member, the elastic abutting slope is abutted against the annular slope so as to resiliently deform the clamping member to change the hole diameter;
wherein the rotating member further comprises:
an end wall comprising a limiting ring groove movably engaged with one end of the body so as to limit relative displacement between the body and the rotating member; and
a side wall connected to the end wall to form an accommodating space, wherein the accommodating space is corresponding to the accommodating seat, the side wall has a sidewall internal thread, the accommodating seat has an accommodating external thread, and the accommodating external thread is correspondingly screwed into the sidewall internal thread;
wherein the replacement seat assembly is configured to replace the abutment assemblies with each other so as to clamp one of the abutment assemblies by the clamping member;
wherein the rotating portion has a rugged surface.

10. The dental clamping apparatus of claim 9, wherein, the rotating member has an internal thread; and
the clamping member has an external thread corresponding to the internal thread, and the external thread is correspondingly screwed into the internal thread.

11. The dental clamping apparatus of claim 10, wherein the rotating member further comprises:
a rotating shaft comprising the annular groove and a rotating hole, and having a cylindrical shape, wherein the internal thread is disposed in the rotating hole, and the rotating hole is located at a front end of the rotating shaft; and
a rotating seat connected to a rear end of the rotating shaft, wherein the rotating seat has the cylindrical shape, and a diameter of the rotating seat is greater than a diameter of the rotating shaft.

12. The dental clamping apparatus of claim 11, wherein, the ball bearing is surroundedly attached to the rotating shaft and connected to the rotating seat, and the ball bearing has a ring shape and a flaky shape; and
the body further comprises a bearing accommodating space, the rotating shaft is passed through the bearing accommodating space, and the ball bearing is disposed in the bearing accommodating space.

13. The dental damping apparatus of claim 9, wherein the ball bearing comprises:
a first annular member connected to the body and synchronously moved with the body;
a second annular member connected to the rotating member and synchronously moved with the rotating member; and
a ball assembly located between the first annular member and the second annular member, wherein the first annular member is moved relative to the second annular member via the ball assembly.

14. The dental clamping apparatus of claim 9, wherein the clamping member further comprises:
a resilient abutting portion comprising the axial track, the elastic abutting slope and the hole diameter, wherein the axial track is parallel to the axial direction, the elastic abutting slope is located outside of the resilient abutting portion, and the hole diameter is located inside of the resilient abutting portion; and
a connecting portion disposed in the through hole, wherein one end of the connecting portion is connected to the resilient abutting portion, and the other end of the connecting portion is movably connected to the rotating member.

15. The dental clamping apparatus of claim 9, wherein the through hole comprises:
a first hole having a first diameter, wherein the first blocking hole is communicated with the first hole and faced towards a first radial direction; and
a second hole communicated with the first hole and having a second diameter, wherein the second diameter is smaller than the first diameter, and the second blocking hole is communicated with the second hole and faced towards a second radial direction.

* * * * *